United States Patent [19]
Speck

[11] Patent Number: 6,129,711
[45] Date of Patent: *Oct. 10, 2000

[54] FLUID-CONTAINING PLASTIC DISPOSABLE SYRINGE THAT IS TO BE STERILIZED AND A PROCESS FOR FILLING AND SEALING SAME

[75] Inventor: Ulrich Speck, Berlin, Germany

[73] Assignee: Schering Aktiengesellschaft, Berlin, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/817,758
[22] PCT Filed: Oct. 27, 1995
[86] PCT No.: PCT/DE95/01523
  § 371 Date: Jun. 19, 1997
  § 102(e) Date: Jun. 19, 1997
[87] PCT Pub. No.: WO96/13289
  PCT Pub. Date: May 9, 1996

[30] Foreign Application Priority Data

Oct. 28, 1994 [DE] Germany ............... 44 39 738

[51] Int. Cl.[7] ................................ A61M 5/32
[52] U.S. Cl. ............ 604/199; 604/110; 604/200; 604/227; 604/263; 141/2; 141/18
[58] Field of Search ................. 604/181, 187, 604/199, 200, 110, 218, 227, 239, 240, 264, 263, 275, 117, 192; 141/2, 18

[56] References Cited

U.S. PATENT DOCUMENTS

| | | | |
|---|---|---|---|
| 3,667,657 | 6/1972 | Chiquiar-Arias | 604/110 |
| 3,828,775 | 8/1974 | Armel | 604/200 |
| 4,051,850 | 10/1977 | Tischlinger | 604/227 |
| 4,981,472 | 1/1991 | Ennis, III et al. | 604/239 |
| 5,009,640 | 4/1991 | Pyret et al. | 604/117 |
| 5,053,020 | 10/1991 | Manchester | 604/239 |
| 5,059,172 | 10/1991 | Sutherland et al. | 604/192 |
| 5,084,017 | 1/1992 | Maffetone | 604/110 |
| 5,147,325 | 9/1992 | Mitchell et al. | 604/192 |
| 5,380,300 | 1/1995 | Pritchard et al. | 604/275 |
| 5,538,506 | 7/1996 | Farris et al. | 604/212 |
| 5,540,666 | 7/1996 | Barta et al. | 604/192 |

FOREIGN PATENT DOCUMENTS

| | | |
|---|---|---|
| 1239061 | 4/1967 | Germany . |
| 0360168 | 3/1962 | Switzerland . |
| 2249727 | 5/1992 | United Kingdom . |

*Primary Examiner*—Ronald K. Stright, Jr.
*Attorney, Agent, or Firm*—Millen, White, Zelano & Branigan

[57] ABSTRACT

A process for filling and sealing a fluid-containing plastic disposable syringe that is to be sterilized, wherein the disposable syringe includes a barrel having a front end, a nozzle part having a sealing element, a plunger plug, and a plunger stop element that is placed in the area of a cylinder gripping plate, the process includes inserting and pushing the plunger plug into the front end of the barrel, using pressure and forcing a fluid medium into the barrel via the nozzle part, whereby the fluid medium pushes the plunger plug in the direction of the plunger stop element, and sealing the sealing element of the nozzle part by plastic deformation after the barrel and the nozzle part are filled.

15 Claims, 4 Drawing Sheets

FLUID-CONTAINING PLASTIC DISPOSABLE SYRINGE THAT IS TO BE STERILIZED AND A PROCESS FOR FILLING AND SEALING SAME

BACKGROUND OF THE INVENTION

1. Field of the Invention

This invention relates to a process for filling and sealing a fluid-containing plastic disposable syringe that is to be sterilized, whereby the disposable syringe comprises a barrel with a nozzle part that is molded at the front, an at least one-piece plunger or plunger plug, and a plunger stop element that is placed in the area of the cylinder gripping plate 2. Description of the Prior Art To date, ampoules and injection vials have primarily been used for parenteral administration of liquid pharmaceutical agents. In addition, a hypodermic syringe with a matching injection cannula is required to administer the liquid or free-flowing substances that are decanted in these containers. This means, however, that the pharmaceutical agent must be transferred to such a hypodermic syringe before final use. This is not only time-consuming but also creates considerable opportunities for contamination.

To keep the liquid pharmaceutical agent from being contaminated, therefore, prefilled disposable syringes are already available on the market. Such a disposable syringe is known from EP-B 0 227 401. There, a process for the production of filled, sterile plastic syringes is described. The disposable syringe, whose design corresponds to DIN 13 098 Part 2, is sterilized in a special process to preserve its geometric shape. To prevent the plastic disposable syringe from being deformed in an autoclave under the action of high internal syringe pressure, the pressure is increased in the autoclave by adding compressed air until the internal syringe pressure is reached.

In addition to a pneumatic pump, this process required a steam generator with low inertia since although the compressed air that is introduced into the autoclave raises the internal autoclave pressure, it considerably lowers the temperature that is necessary for sterilization. It is also disadvantageous that heat transfer is reduced by the presence of air in the air/vapor mixture, which leads to a prolonged retention time in the autoclave.

Another drawback arises from the design of the disposable syringe that is used. It must be filled with the preparation through the opening on its plunger rod side. With this method of filling, a gas bubble is included in the barrel under the plunger plug that is to be used which further increases the internal syringe pressure during sterilization and thus forces the plunger plug to be pushed out and/or the syringe body to deform.

This drawback also exists for a subcutaneous syringe with a partial glass structure that is known from U.S. Pat. No. 5,069,670. The syringe has a glass barrel, a mounted cylinder gripping plate with an internal collar, a mounted head element with a standard connecting part for attaching medical cannulae, a plunger plug, and a sealing part. It cannot be sterilized in the filled state, however, since its glass cylinder cannot withstand high internal pressure during a sterilization process in the autoclave.

SUMMARY OF THE INVENTION

This invention therefore focuses on the problem of developing a process for filling and sealing a fluid-containing plastic disposable syringe that is to be sterilized, by which the disposable syringe can be sterilized in the filled state in a standard type of autoclave, without the danger arising of plastic deformation owing to the internal syringe pressure of the syringe parts. In this case, the disposable syringe is to be configured in such a way that largely gas-free filling is made possible. Further, the syringe components are to be simple to clean and to handle. Also, the drawbacks that are known from the area of prior art are to be avoided.

The problem is resolved, i.e., by virtue of the fact that the plunger or plunger plug, after insertion into the empty barrel, is inserted all the way up to its front end with or without the specific plunger rod and then the fluid medium is forced into the barrel under pressure via the nozzle part, whereby the fluid medium pushes the plunger or plunger plug in the direction of the plunger rod side up to the plunger stop element. After filling, the front area of the nozzle part is sealed by plastic deformation.

With this process, the disposable syringe can be filled almost gas-free. The filling device is connected to the front, open end of the sealing element to force the preparation that is subjected to pressure via the nozzle part into the interior of the syringe body. Because of the plunger plug that is attached in the nozzle area, the preparation cannot flow freely into the barrel, but has to push the plunger plug forward, optionally with the plunger rod. As a result, i.e., foaming of the preparation is prevented, so that after the filling device is detached, only a few gas bubbles are present in the barrel. For the most part, the gas comes from the cavity of the nozzle part. As the disposable syringe is being moved to the next processing station, the gas rises and collects in the upper area of the nozzle part. Theoretically, the liquid level should then have to lie at the lower edge of the nozzle part when the disposable syringes are arranged vertically. Since the preparation was filled under pressure, however, on the one hand the syringe body has expanded slightly, and, on the other hand the plunger plug has been minimally compressed. Both elastic deformations heal themselves, causing the liquid level in the nozzle part to rise almost to the upper edge. Optionally, the rising of the gas bubbles into the front or upper nozzle part is supported by an ultrasonic generator or the like.

The plunger plug can also partially project into the nozzle part, thereby reducing the residual gas volume there.

Within the scope of the process, the disposable syringe is sealed in such a way that the front area of the nozzle part, for example, is plastically deformed with partial heat input. In this case, welding and gluing processes can be used.

To complete the process, a protective cap is optionally put on over the nozzle part. The protective cap is attached to the nozzle part or the barrel by friction and/or clamping. It protects the relatively thin and thin-walled nozzle part against mechanical damage.

In its rear area, the nozzle part preferably has the shape of a connecting part with an outer cone according to German Industrial Standard (Dentscre Industrie Normen) DIN 13 090 with or without a locking part.

If the rear area of the nozzle part is only a conical connecting part according to German Industrial Standard (Dentscre Industrie Normen) DIN 13 090, Part 1, the above-mentioned protective cap is pushed on to attach it to the outer cone of the connecting part.

The front area of the nozzle part is approximately a tubular sealing element that projects over the standard connecting part. The so-called sealing element is at least three times longer than the connecting part. It is used, on the one hand, for adapting the syringe body to the filling device and collecting the residual gas that remains after filling in the syringe body and, on the other hand, for sealing the syringe body on the nozzle side.

The nozzle part has a throat in the area between the connecting part and the sealing element. In this throat is mounted the tool for separating the connecting part and sealing element before the preparation is administered. The throat is placed and configured in such a way that after the sealing element is separated, the standard connecting part for attaching the medical devices that are to be connected later is created.

Despite the throat, the inner wall of the sealing element merges without a seam and without a change in size into the inner wall of the connecting part, so that there is no fluidic or bubble-forming obstacle is created.

The throat can also be designed as a predetermined point of break with high notching action, i.e., when brittle materials are used. In this case, the sealing element can be separated from the connecting part by being twisted off and/or broken off.

The plunger stop element is a separate component that projects with at least one plunger support element into the barrel or covers the barrel, and engages the cylinder gripping plate from behind with at least one gripping element. With the aid of the plunger stop element, the plunger or the plunger plug is kept from being pushed out from the barrel during filling and autoclaving of the disposable syringe. For this purpose, the plunger stop element can be mounted on, for example, the cylinder gripping plate, whereby locking elements secure the plunger stop element to the cylinder gripping plate or the barrel.

Another alternative consists in shaping in the rear end of the barrel knobs which project inward and on which the plunger can be supported. To do this, the plunger must have recesses in the bottom of the plunger or the plunger base that correspond to the knobs, whereby the recesses are arranged spaced around the periphery of the plunger like the knobs on the inner wall of the cylinder. After insertion into the barrel, the plunger is swung around a half spacing around its longitudinal axis, so that the plunger bottom areas without a recess coincide with the knobs.

The plunger stop element is equipped with recesses at least in the area of the barrel, so that there are no closed cavities between the plunger and the plunger stop element. Such cavities could partially produce heating that is inadequate for sterilization during autoclaving owing to their thermal insulating action.

The same problem also exists for the protective cap with the subjacent nozzle part. To ensure that the nozzle part is heated adequately, the protective cap has recesses outside of its attachment area.

The recesses and breaks also make it possible for the disposable syringe to dry completely after autoclaving.

Owing to the small volume flow due to factors related to the cross-section, filling the disposable syringe via the nozzle part takes more time than filling the barrel at the back. To ensure that the cycle time of the conventional filling process is maintained, several filling devices are preferably charged in parallel.

BRIEF DESCRIPTION OF THE DRAWINGS

Other details of the invention emerge from the embodiment that is described and depicted diagrammatically below.

DETAILED DESCRIPTION OF THE DRAWINGS

Figure 1:
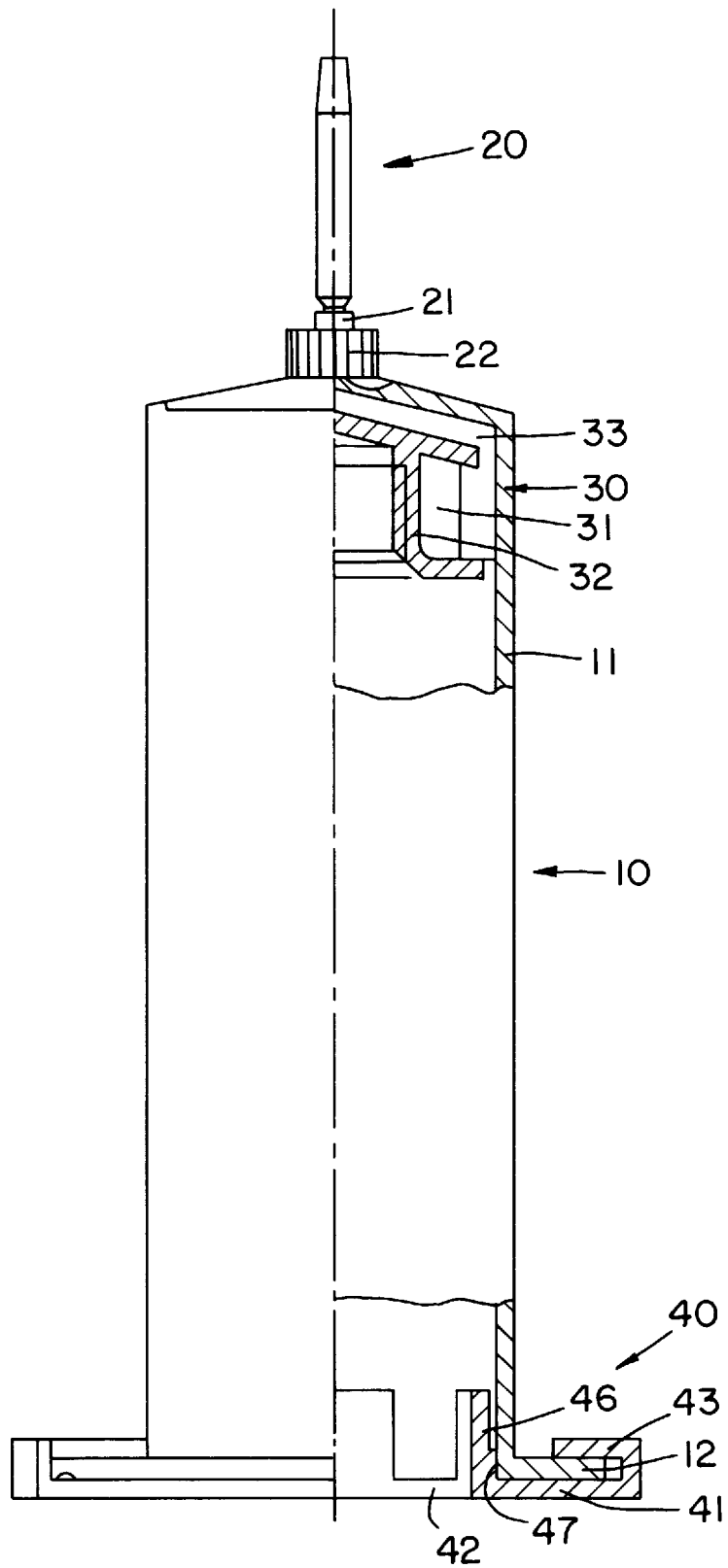
FIG. 1: Partially cut-away side view of the mounted disposable syringe before filling.

FIG. 1 shows a large-volume disposable syringe, which, apart from a special nozzle part (20) and a plunger stop element (40) of German Industrial Standard (Dentscre Industrie Normen) DIN 13 098, Part 1, corresponds to a plastic disposable syringe. Accordingly, its syringe body (10) consists of a barrel (11) with a cylinder gripping plate (12) that is molded at the rear end and a lockable connecting part (21) that is placed at the front end with an outer cone according to German Industrial Standard (Dentscre Industrie Normen) DIN 13 090, Part 2. Connecting part (21), however, within the framework of the invention, i.e., is designed extended. A plunger plug (30) is located in barrel (11). This plunger plug (30) consists of a plunger seal (33) that is put on plunger base (31) and has inner threading (32). Inner threading (32) is used to attach the plunger rod, not shown. Plunger base (31) projects at its rear end in the longitudinal direction of the syringe over plunger seal (33) to form a defined support for resting on plunger stop element (40).

Figure 3:
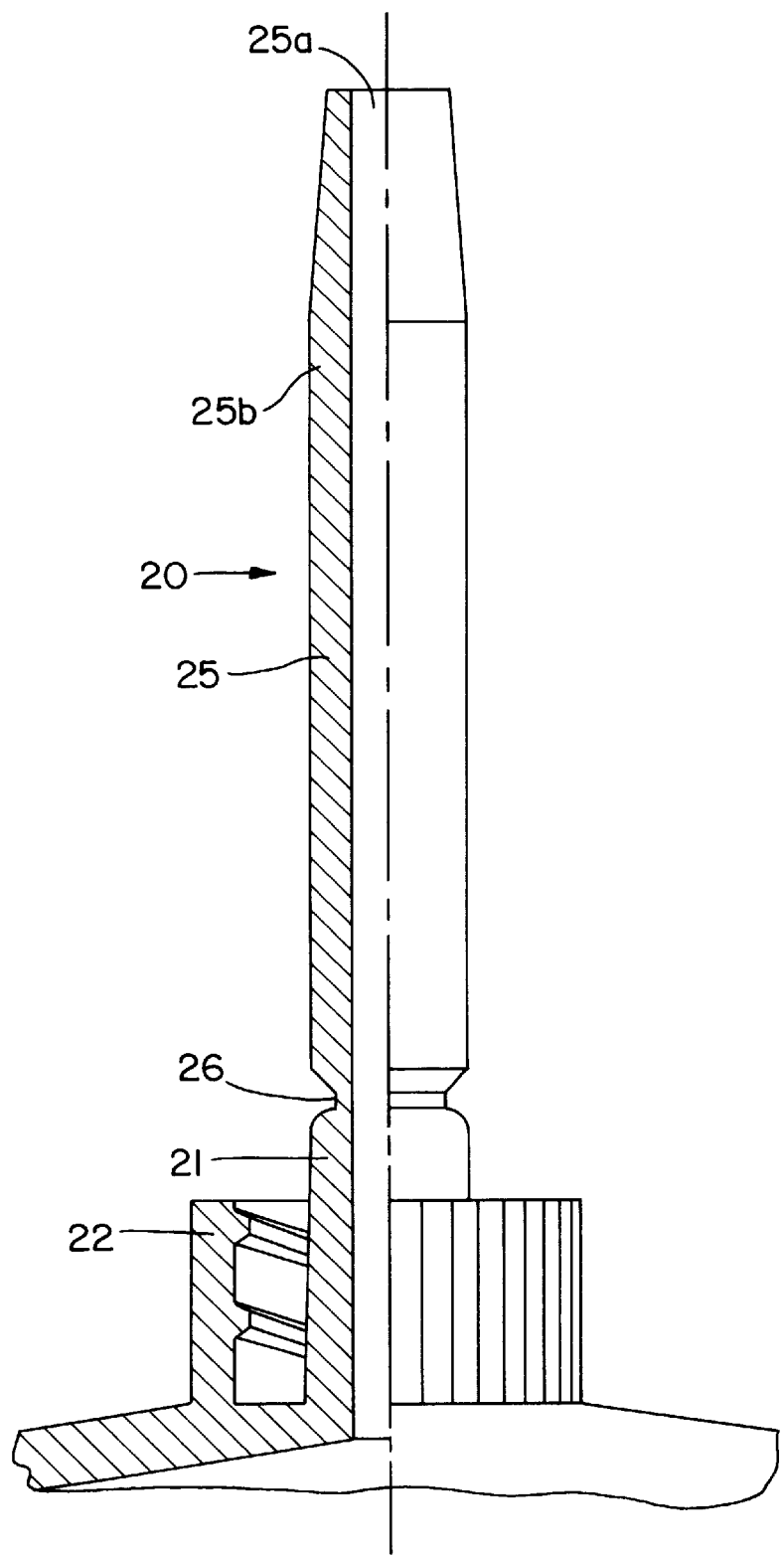
FIG. 3: partially cut-away side view of the nozzle part with a Luer lock connecting part before the disposable syringe is filled.

In FIG. 3, nozzle part (20) of the unfilled disposable syringe is presented in enlarged form. In addition to standard locking part (22) and conical connecting part (21), it has, i.e., an extension that is provided for filling. The extension, which is about 3 times as long as connecting part (21), is a so-called sealing element (25) which initially has an open free end 25a and a sealing portion 25b. A throat (26) separates sealing element (25) and connecting part (21). Behind connecting part (21), the side of throat (26) is an outer radius that is adapted to the shape of connecting part (21). The base of the throat is cylindrical. There, the wall thickness is less than a half millimeter. Behind sealing element (25), the side of the throat is a 45° bevel.

At its front end, sealing element (25) has an outer cone with a 1:4 slope. The inner wall of entire nozzle part (20) is approximately cylindrical.

Figure 2:
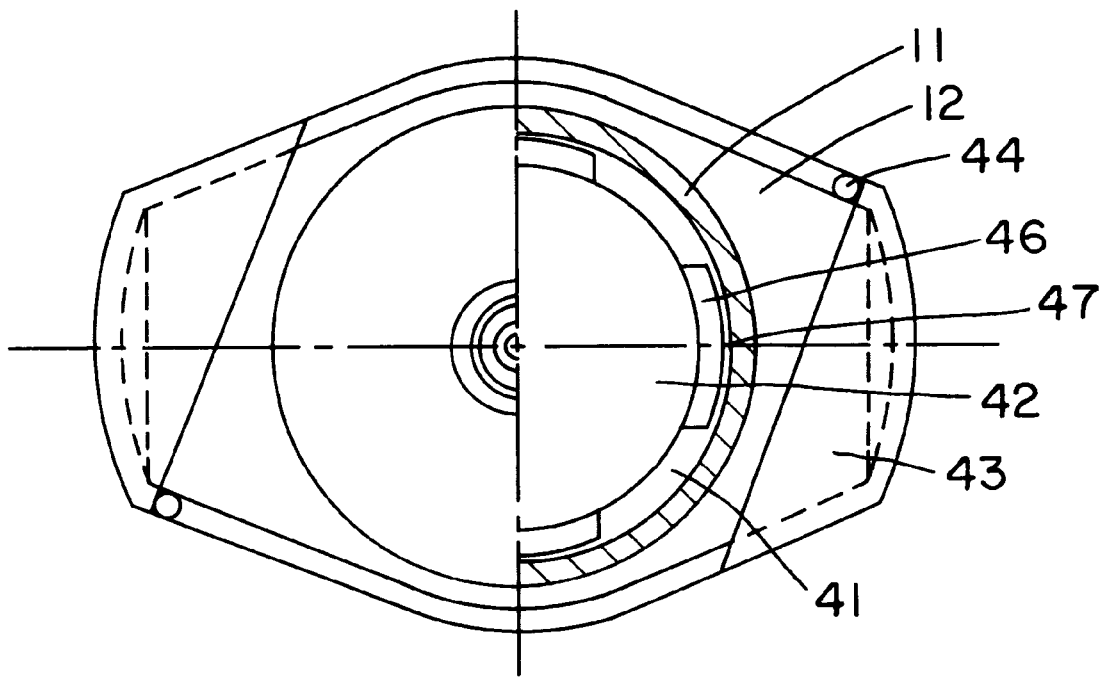
FIG. 2: top view of the partially cut-away, mounted disposable syringe.

Plunger stop element (40) is located at the other end of the disposable syringe in barrel (11), see. FIGS. 1 and 2. It comprises a base plate (41), on which, on the one hand, four plunger support elements (46) that project into barrel (11) are located, and, on the other hand, there are two gripping elements (43), which at least partially engage cylinder gripping plate (12) on the outside. Plunger support elements (46) are molded at equidistant intervals around a central hole (42) of base plate (41). Each of the plunger support elements (46) has, over its entire length, a cross-section that largely corresponds to the shape of a circular ring section. The outer contour of the circular ring cross-section has about the length of ⅛ the circumference. The uncurved lateral surfaces of plunger support elements (46) form planes that run parallel around half the width of plunger support elements (46), offset to the assumed center line of the disposable syringe. Plunger support elements (46) that are aligned parallel to the wall of barrel (11) do not touch the wall itself. This has, i.e., the advantage that after sterilization, these zones dry quickly.

Centering elements (47) are located between plunger support elements (46) and the wall of barrel (11). The centering elements are located on the outer contour of plunger support elements (46) in the area of cylinder gripping plate (12). They are aligned parallel to the center line of the syringe and midway to respective plunger support element (46). Their cross-section is approximately semicircular.

Base plate (41), whose center hole (42) is also used to guide the plunger rods, not shown, completely covers cylinder gripping plate (12) from the outside. In this case, it projects slightly over the edge of cylinder gripping plate (12). The projecting edge is designed to be circular in sections in the area that is the farthest from the center line of the syringe. In this edge area, gripping elements (43) are molded-on. In both halves of cylinder gripping plate (12), the shapings also extend, as FIG. 2 shows, in the direction of barrel (11). Corresponding to FIG. 2, this is on the right half in the lower area and in the left half in the upper area. Gripping elements (43) partially engage the lower side of cylinder gripping plate (12) from the outside, so that the lower side on both halves is obliquely covered in each case. The shape of the plunger stop element is partially determined by the type of assembly. Plunger stop element (40) is, like a bayonet catch, first inserted into the barrel and then brought into the gripping position, relative to the direction of insertion, by a clockwise rotation by 90°. To this end, plunger stop element (40) is used in barrel (11) rotated by 90° relative to the center line of the syringe in the assembly compared to the illustrations in FIGS. 1 and 2. Plunger stop element (40) reaches the position shown only by clockwise rotation. For attaching in this gripping position, in each case two safety knobs (44) are placed on the edge of two gripping elements (43). They prevent any unintentional reversal of plunger stop element (40).

Before the disposable syringe is filled and after the sterilization of the individual parts and the application of lubricant on the inner wall of the barrel, plunger plugs (30) are inserted into syringe body (10) and pushed up to the front end of the barrel. Then, plunger stop element (40) is inserted and swiveled to secure it. When plunger plug (30) and/or plunger stop element (40) is inserted, depending on design, the original plunger rod can also be mounted. When plunger plug (30) is inserted, plunger stop element (40) can even sit loosely on the plunger rod.

For filling the disposable syringe, for example, the filling nozzle of the decanting machine that is equipped with an inner cone is mounted on the outer cone of sealing element (25). During the filling process, plunger plug (30) is pushed by the liquid preparation that is pressed into barrel (11) in the direction of plunger stop element (40). As soon as plunger plug (30) rests on plunger stop element (40), the filling process is completed, and the filling nozzle rises from sealing element (25). As the disposable syringe is being moved to the next processing position, gas bubbles that are included in the preparation by shaking during shipment or by any additional vibration rise and collect in the front area of sealing element (25). As heat is input, the front part is crushed, twisted off, or similarly tightly sealed with plastic deformation.

Figure 4:
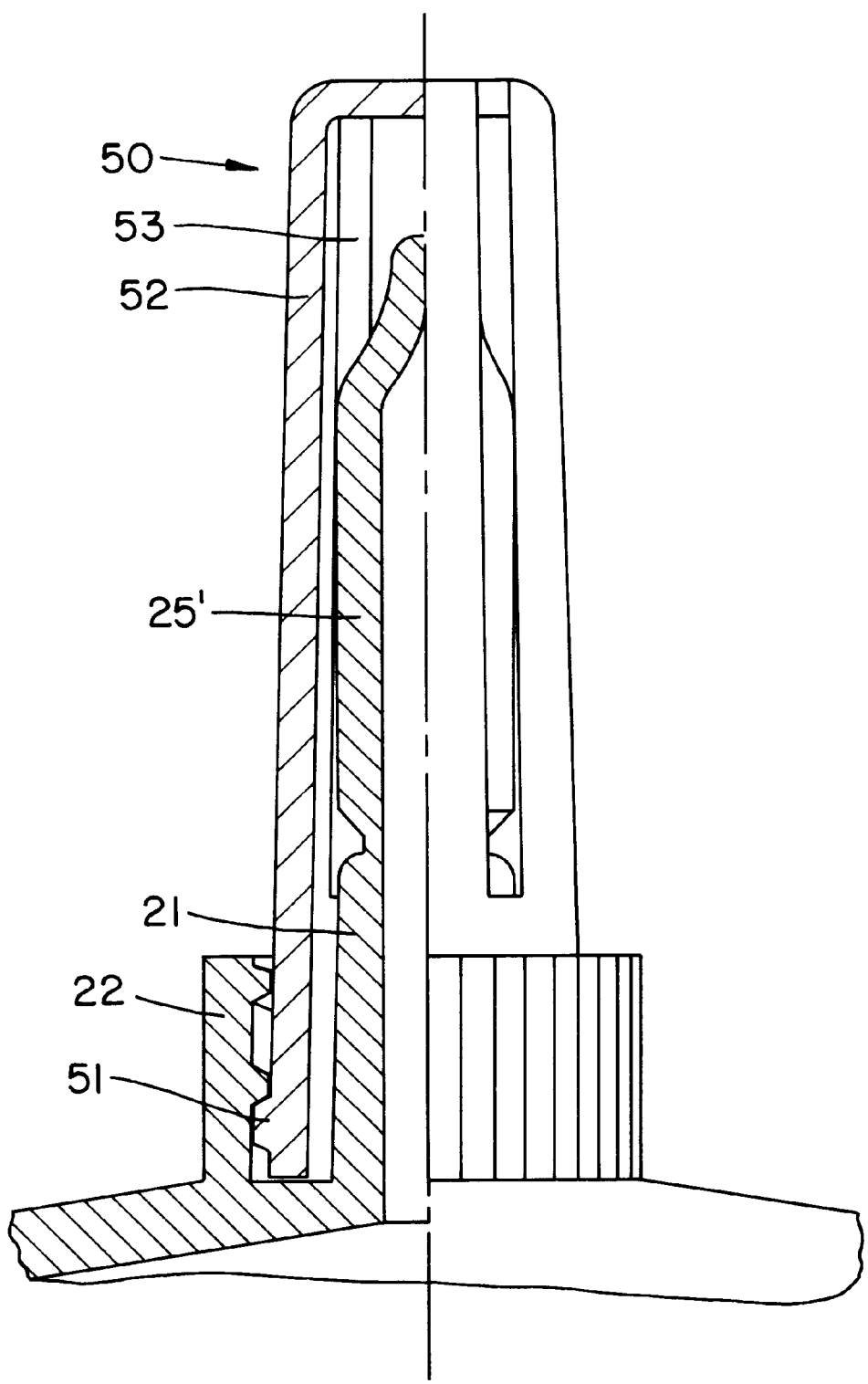
FIG. 4: partially cut-away side view of the nozzle part after the disposable syringe is filled and sealed.

Deformed sealing element (25') is shown in FIG. 4. A frustum-like protective cap (50) is put over sealing element (25') and screwed tight with the aid of the threading that is integrated in locking part (22). To this end, two short threaded sections (51) are located on the lower edge of protective cap (50), as indicated by, for example, German Industrial Standard (Dentscre Industrie Normen) DIN 13 090, Part 2, compare connecting part Luer-Lock (LLS) with shapes set forth in the Germnan Industrial Standard. Protective cap (50) has a wall (52) and four recesses (53) that are arranged symmetrically to the center line of the syringe and extend over ¾ of the length of the protective cap.

To prepare the disposable syringe for use, protective cap (50) is screwed off, and sealing element (25') is separated from conical connecting part (21). The separation in the area of throat (26) can be done with the aid of shears, a knife, a scalpel, or the like. After sealing element (25') is separated, nozzle part (20) to is available for attaching an injection element.

LIST OF REFERENCE SYMBOLS

10 Syringe body
11 barrel
12 cylinder gripping plate
20 nozzle part
21 conical connecting part
22 locking part
25 sealing element, undeformed
25' sealing element, deformed
26 throat
30 plunger plug, plunger
31 plunger base
32 thread for plunger rods
33 plunger seal
40 plunger stop element
41 base plate
42 hole, central
43 gripping elements
44 safety knobs
46 plunger support elements
47 centering elements
50 protective cap
51 threaded section
52 wall
53 recesses

What is claimed is:

1. A fluid-containing plastic disposable syringe that is to be sterilized, comprising:
    a barrel having a front end and a gripping-plate end with a gripping plate disposed thereon;
    a nozzle part molded with said barrel at the front end of said barrel; said nozzle part having a deformable sealing portion, a connecting part, and an open free end, the free end adapted to receive therethrough a pressurized fluid medium which fills the barrel;
    a plunger-plug placed inside of said barrel; and
    a plunger-stop element placed adjacent to said gripping plate, the plunger-stop element engaging the plunger-plug to prevent the plunger plug from being pushed out of the barrel at the gripping-plate end by the pressurized fluid medium during filling of the barrel, wherein the fluid medium is retained within the barrel by deforming the sealing portion to close the nozzle part.

2. A disposable syringe according to claim 1, wherein said connecting part comprises an outer cone.

3. A disposable syringe according to claim 2, wherein said connecting part with said outer cone comprises a locking part.

4. A disposable syringe according to claim 1, further comprising a protective cap with an attachment area, said protective cap being removably attached to said nozzle part.

5. A diposable syringe according to claim 4 wherein outside of its attachment area said protective cap has recesses therethrough.

6. A disposable syringe according to claim 1, wherein said sealing portion is substantially tubular.

7. A disposable syringe according to claim 1, wherein said nozzle part has a throat between said connecting part and said front area.

8. A disposable syringe according to claim 1, wherein said plunger-stop element comprises at least one plunger support element extending into said barrel and engaging behind said gripping plate with at least one gripping element.

9. A disposable syringe according claim 1, further comprising a protective cap with an attachment area, said protective cap being removably attached to said barrel.

10. A disposable syringe according to claim 1, wherein said plunger-stop element comprises at least one plunger support element covering said barrel and engaging behind said gripping plate with at least one gripping element.

11. A process for filling and sealing a fluid-containing plastic disposable syringe that is to be sterilized, comprising:

providing a disposable syringe having a barrel with a front end and an open rear end, a hollow nozzle part having a front area with an open free end, a plunger plug and a plunger stop element that is placed in the area of a cylinder gripping plate disposed at the rear end of the barrel, inserting and pushing the plunger plug from the open rear end to the front end of the barrel;

forcing a fluid medium through the open free end of the nozzle part by using pressure applied to the fluid medium, to thereby fill the barrel as the fluid medium propelled by the pressure pushes the plunger plug toward the plunger stop element at the rear end of the barrel; and after filling the barrel with the fluid medium, sealing said front area of the nozzle part by plastic deformation.

12. The process according to claim 11 wherein the syringe is oriented vertically during the process; wherein gas bubbles collect in the front area of the nozzle part, and wherein sealing the front area separates the gas bubbles from the fluid medium.

13. The process of claim 12 further including separating the front area of the nozzle part from the syringe.

14. The Process according to claim 11, wherein scaling said front area of the nozzle part by plastic deformation is achieved by heat input applied to the nozzle part.

15. The process according to claim 11, further comprising: placing a protective cap over the nozzle part and attaching the protective cap to the nozzle part.

* * * * *